United States Patent
Pastore

(10) Patent No.: US 9,662,671 B2
(45) Date of Patent: May 30, 2017

(54) DEVICE FOR THE DELIVERY OF DISINFECTANTS OR SIMILAR

(71) Applicant: NOCOSYSTEM S.R.L., Castiglione Olona (VA) (IT)

(72) Inventor: Maurizio Pastore, Castiglione Olona (VA) (IT)

(73) Assignee: AMIL CARE CORP., Miami, FL (US)

( * ) Notice: Subject to any disclaimer, the term of this patent is extended or adjusted under 35 U.S.C. 154(b) by 0 days.

(21) Appl. No.: 14/401,694

(22) PCT Filed: May 17, 2013

(86) PCT No.: PCT/IB2013/054049
§ 371 (c)(1),
(2) Date: Nov. 17, 2014

(87) PCT Pub. No.: WO2013/175369
PCT Pub. Date: Nov. 28, 2013

(65) Prior Publication Data
US 2015/0151313 A1  Jun. 4, 2015

(30) Foreign Application Priority Data

May 21, 2012  (EP) ..................................... 12168627
May 31, 2012  (IT) .............................. PC2012A0017

(51) Int. Cl.
*A61L 9/14*   (2006.01)
*B05B 7/24*   (2006.01)
(Continued)

(52) U.S. Cl.
CPC ............ *B05B 7/2491* (2013.01); *A61L 2/186* (2013.01); *A61L 2/22* (2013.01); *A61L 9/14* (2013.01);
(Continued)

(58) Field of Classification Search
CPC .. A61L 2/186; A61L 2202/11; A61L 2202/25; A61L 2209/211; A61L 9/14; B05B 7/2491; B05B 7/2494
(Continued)

(56) References Cited

U.S. PATENT DOCUMENTS 3,425,407 A    2/1969 Furman et al.
3,643,685 A *  2/1972 Hays ....................... F16K 1/126
                                                        137/501
(Continued)

FOREIGN PATENT DOCUMENTS

AU    462 977 B2    7/1975
AU    462977 B2 *  7/1975  .......... A01M 7/0089
(Continued)

OTHER PUBLICATIONS

International Search Report, dated Oct. 29, 2013, from corresponding PCT application.

*Primary Examiner* — Arthur O Hall
*Assistant Examiner* — Joseph A Greenlund
(74) *Attorney, Agent, or Firm* — Young & Thompson

(57) ABSTRACT

A device for the delivery of a liquid in spray form includes a motor (2) connected to a fan (3, 4) adapted to draw a flow of air and send it through at least one conduit (5, 5b), a pre-loading vessel (11) for containing a liquid to be atomized, at least one nozzle (6) located at one end of the conduit (5, 5b) for the delivery of the liquid in spray form, at least one siphoning pipe (14) with one end located inside the pre-charging vessel (11) and an opposing end located in the vicinity of the nozzle (6), and at least one pressure pipe (18) connected to the fan (3, 4) to provide a specific amount of pressurized air to the inside of the pre-charging vessel (11), characterized in having regulating elements (19, 29) adapted to regulate the pressure inside the pre-charging vessel (11).

20 Claims, 2 Drawing Sheets

(51) Int. Cl.
*A61L 2/22* (2006.01)
*A61L 2/18* (2006.01)

(52) U.S. Cl.
CPC .......... *B05B 7/2416* (2013.01); *B05B 7/2494* (2013.01); *A61L 2202/11* (2013.01); *A61L 2202/25* (2013.01); *A61L 2209/211* (2013.01)

(58) Field of Classification Search
USPC ..................................... 239/77, 78, 373, 366
See application file for complete search history.

(56) References Cited

U.S. PATENT DOCUMENTS

| | | | | |
|---|---|---|---|---|
| 3,648,401 | A * | 3/1972 | Stains | A01M 7/0014 43/129 |
| 3,793,762 | A * | 2/1974 | Stains | B05B 7/0416 239/77 |
| 3,903,968 | A * | 9/1975 | Livingston | A62C 5/002 169/14 |
| 3,971,409 | A * | 7/1976 | Bauer | G05D 16/0658 137/510 |
| 4,193,547 | A * | 3/1980 | Ballu | B05B 9/06 222/614 |
| 4,194,650 | A * | 3/1980 | Nottke | B01F 15/0416 222/133 |
| 4,222,521 | A * | 9/1980 | Nielsen | B08B 3/026 137/588 |
| 4,235,373 | A * | 11/1980 | Clark | A61L 9/14 239/120 |
| 4,520,993 | A * | 6/1985 | Schertler | F16K 7/07 251/334 |
| 5,031,834 | A * | 7/1991 | Simpson | A01M 7/0082 169/15 |
| 5,133,500 | A * | 7/1992 | Simpson | B05B 7/262 239/150 |
| 5,320,252 | A * | 6/1994 | Fleming | B67D 7/72 222/145.1 |
| 2007/0034095 | A1 * | 2/2007 | McDonnell | A61L 2/202 99/468 |
| 2009/0250532 | A1 * | 10/2009 | Ganan Calvo | B05B 7/1686 239/137 |
| 2010/0123018 | A1 * | 5/2010 | Sardo | A23B 7/153 239/1 |
| 2012/0111961 | A1 * | 5/2012 | Arnold | A01M 7/0014 239/1 |

FOREIGN PATENT DOCUMENTS

| | | |
|---|---|---|
| DE | 10 2009 027805 A1 | 1/2011 |
| FR | 2 912 328 A1 | 8/2008 |
| JP | 2002 282743 A | 10/2002 |

\* cited by examiner

DEVICE FOR THE DELIVERY OF DISINFECTANTS OR SIMILAR

The present invention relates to a device for the diffusion of a liquid in spray form and more specifically to a device for diffusing a disinfectant liquid or similar in an enclosed space to be sanitized or disinfected.

The present invention relates to the disinfection and sanitization of critical environments. More specifically, the invention relates above all to the disinfection and sanitization of surgical instruments and/or medical equipment such as those found in operating theaters, intensive care units, dental surgeries or hospital wards, and the furniture present in these areas. The device according to the invention may also be effectively used for the disinfection of pharmaceutical research laboratories, and food production, storage and processing areas.

Currently, sanitization and disinfection operations in many hospitals are still carried out in a fully manual manner. The procedure involves the use of disinfectant liquid solutions that are distributed over the surfaces of furniture and equipment by means of cloths or similar, and are then dried.

These procedures, in addition to requiring a considerable number of personnel, are also inefficient, particularly due to the difficulty of reaching less accessible areas of the room manually.

Devices are known on the market for the diffusion in droplet spray form of disinfectant liquids that can reach practically every area and every surface of a room to be sanitized and disinfected.

A very fine spray (with droplets with a diameter of less than 5 microns) makes it possible to uniformly diffuse the product without wetting the surfaces and therefore without any need for subsequent manual intervention.

For example, there is the known use of hydrogen peroxide disinfectants, which due to their oxidizing power are capable of eliminating practically all pathogenic micro-organisms present both on the surfaces of equipment and furniture, and in the air inside the room.

However, to achieve this, in other words in order for the disinfectant to be able to act effectively, a specific quantity of disinfectant product needs to be delivered inside the room, based on its volume.

In other words, the disinfectant action of the product varies according to its percentage with respect to the amount of air in the room and, specifically, increases as the amount of air increases until it reaches a maximum threshold beyond which it could be detrimental to equipment and furniture, but also to people (due to corrosion, etc.).

A problem encountered with known diffusion devices is that of being able to deliver exactly the quantity of disinfectant product required according to the size of the room.

In particular, the problem encountered is that of ensuring that a minimum quantity of disinfectant is always or in any case delivered (to ensure the elimination of most microorganisms), without exceeding the necessary amount or delivering quantities that could be harmful for things or for people who enter the room once the disinfection procedure has been completed.

Patent application FR 2912328 A1 describes a liquid diffusing device with a Venturi effect that can expel the liquid in spray form by means of a nozzle that also acts as a support for the flask containing the liquid.

This expulsion is achieved by means of an electric motor connected to a fan, on the end of which is fitted the nozzle which, thanks to the Venturi effect, is able to expel the liquid that is drawn through an injector immersed in the flask of liquid.

The flow of liquid spray delivered by these types of devices is determined mainly by the design parameters such as the size of the Venturi nozzle and the flow of air moved by the fan.

Once calibrated, a device of this type delivers a quantity of air that in theory is almost constant and known over time. To know how long the device needs to remain in operation to deliver the correct quantity of disinfectant product depending on the size of the room to be disinfected, the total quantity of product to be delivered is divided by the product flow rate over time.

The problem that afflicts these known devices, or those devices that atomize the liquid by means of a Venturi nozzle, is that the flow of liquid effectively delivered is subject to considerable variations caused by multiple factors.

Mainly, the flow of liquid drawn from the liquid container varies according to the outside pressure which, acting on the free surface of the liquid in the container, affects the thrust of the liquid in the conduit drawing the liquid towards the nozzle. This problem occurs especially, for example, when the machine is used in places at an altitude that is notably different with respect to the altitude at which the machine was designed and calibrated.

In the same way, other environmental parameters such as temperature and humidity can cause considerable variations in the flow of liquid delivered in spray form.

Lastly, in the case of variations or drops in the electrical power supply, the device may be subject to variations in the rotation speed of the electric motor, which can result in variations in the speed of the flow of air delivered and therefore on the flow of liquid that the Venturi nozzle is able to draw from the flask.

When using known devices, in order to be sure that at least the minimum indispensable quantity of disinfectant is delivered, it is therefore normal practice to increase the treatment time beyond that specified, resulting in an unnecessary waste of product and the risk of delivering an excessive quantity that could be harmful for persons or things.

Patents AU 462977 B2 and DE 102009027805 A1 describe further devices for the diffusion of a liquid spray in which a conduit connected by means of fans communicates with the portion of the liquid container occupied by air, in order to pressurize the liquid which is delivered through one or more nozzles.

These known devices also have certain limitations.

In fact, both work with a liquid pressure that is determined mainly by the flow of air introduced through the conduit into the container. Since these devices generally work with fixed-speed centrifugal fans, it is not possible to regulate the flow of liquid delivered and therefore to calibrate the device according to requirements, with the same disadvantages as described above.

In this context, the aim of the present invention is to provide a device for the diffusion of a disinfectant liquid which overcomes the problems associated with known art described above.

In particular, the aim of the present invention is to provide a device for the diffusion of a disinfectant liquid in spray form capable of delivering a precise and constant amount of the product, in all environmental conditions.

In detail the aim of the present invention is to create a device for the diffusion of a disinfectant liquid in spray form that enables a determined flow of liquid to be delivered for a given environment, in different conditions of pressure, temperature, humidity or other parameters relating to the room to be disinfected.

A further aim of the present invention is to create a device for the diffusion of a disinfectant liquid in spray form that is reliable, economical and does not have substantial complications with respect to known devices.

These aims are achieved by a device for the delivery of a liquid in spray form comprising a motor connected to a fan adapted to draw a flow of air and send it through at least one conduit, a pre-charging vessel for containing a liquid to be atomized, at least one nozzle located at one end of said conduit for the delivery of said liquid in spray form, at least one siphoning pipe with one end located inside said pre-charging vessel and an opposing end located in the vicinity of said nozzle, at least one pressure pipe connected to said fan to deliver a specific amount of pressurized air to the inside of the pre-charging vessel, characterized in having regulating means adapted to regulate the pressure inside said pre-charging vessel.

Said flow of air injected into the pre-charging vessel ensures that a pressure is exerted on the free surface of the liquid that is always higher than the atmospheric pressure, which forces the liquid to rise through the siphoning pipe towards the nozzle.

Thanks to these regulating means, it is therefore possible to regulate this excess pressure inside the pre-charging vessel and thereby to vary the flow of liquid delivered by the device's nozzles.

More specifically, said regulating means are configured to regulate the speed, and therefore the pressure, of a flow of air entering or exiting said pre-charging vessel, thereby varying the pressure value inside it.

According to a first variant of the invention, these regulating means comprise a bleed valve that can be adjusted to allow a certain quantity of air to be released to the outside.

Said bleed valve is preferably located at the end of a bleed pipe, which in turn communicates with the pre-charging vessel.

In another variant of the invention, said regulating means may comprise a regulating valve located on the pressure pipe.

More specifically, said valve is configured to vary the speed of the flow of air entering the pre-charging vessel, and therefore the internal excess pressure.

Preferably said regulating valve is configured to vary the cross-section of the pressure pipe.

By measuring both the total flow of air and liquid delivered by the nozzles, and the quantity of liquid consumed in a given period of time, it is possible to establish whether the device is capable of delivering the required quantity of liquid product.

If it is not, in order to calibrate the device to deliver the correct quantity, it is sufficient to act on said regulating means to increase or decrease the flow of liquid. This operation can therefore be carried out periodically as required by certain standards, or each time the device is used in different environmental conditions.

Further characteristics and advantages will become more apparent from the following description of a preferred embodiment of the invention, which is illustrated by no way of limitation in the accompanying drawings, in which.

Figure 1:
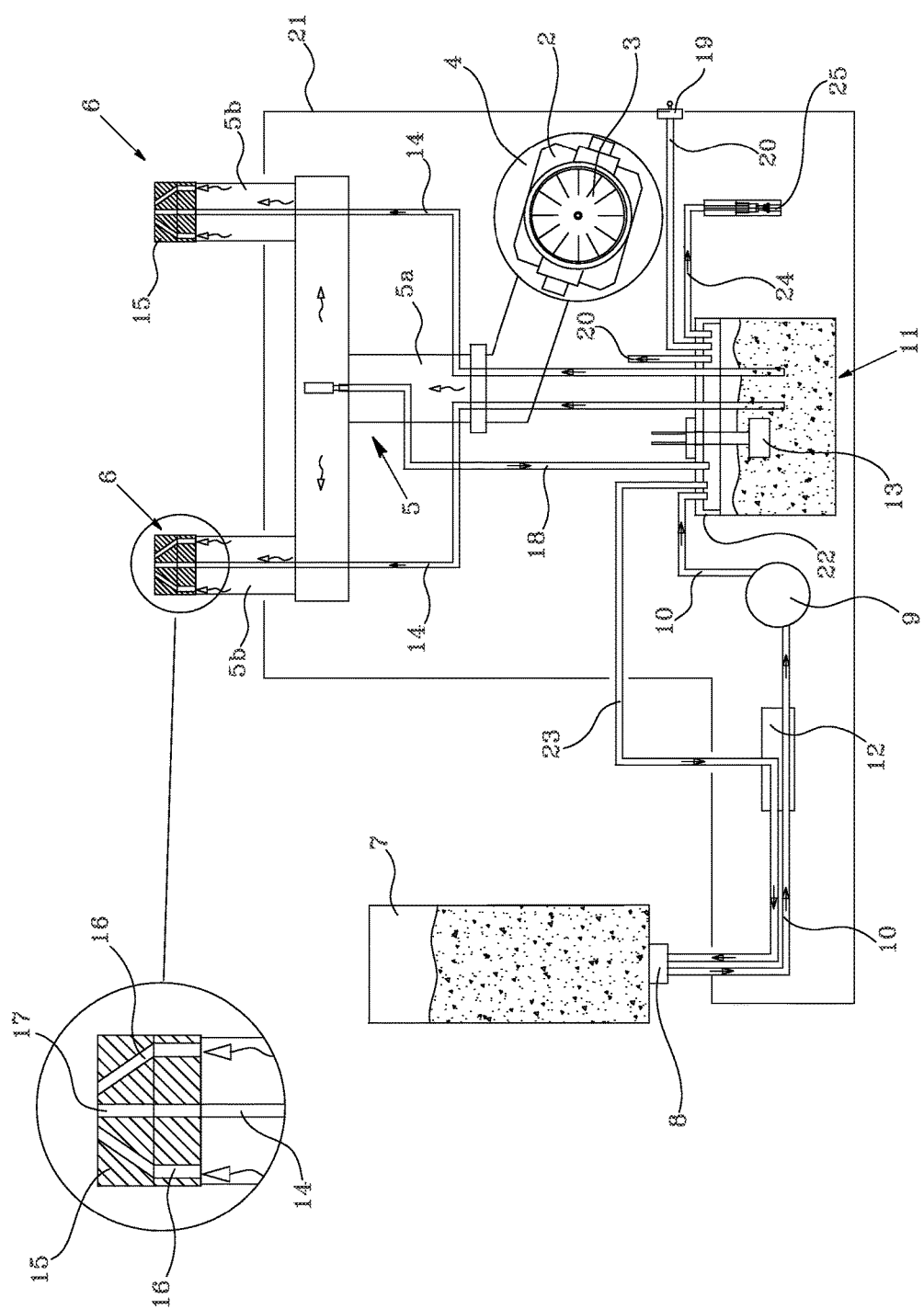
FIG. 1 shows a schematic side view of the device for the delivery of a liquid in spray form, according to a first variant of the invention.
Figure 2:
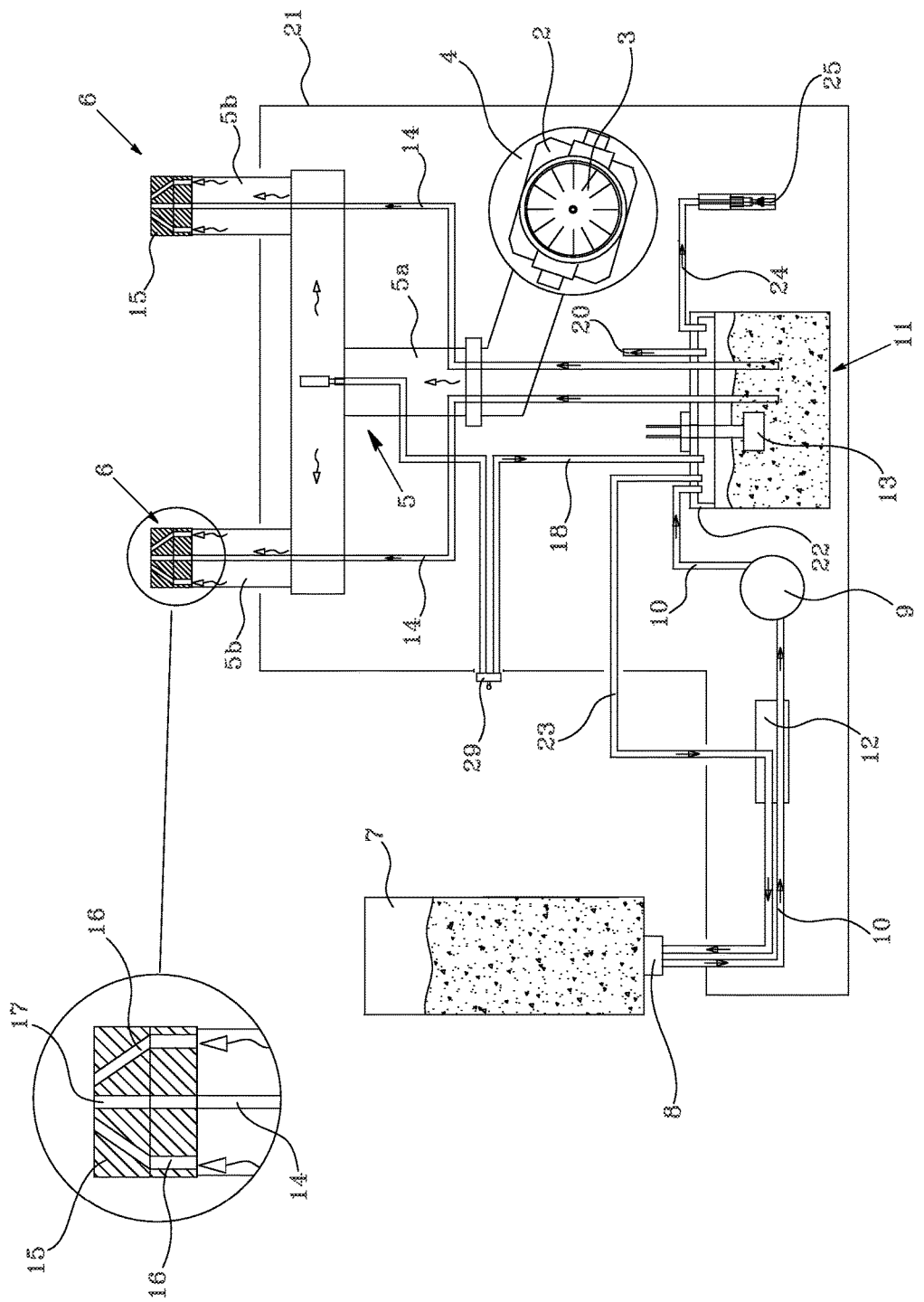
FIG. 2 shows a side view of the device for the delivery of a liquid in spray form, according to a further variant of the invention.

With reference to the accompanying figures, the device for the delivery of a disinfectant liquid, indicated by the number 1, comprises a motor 2 connected to a fan unit for aspirating and moving a certain flow of air taken from the environment.

In detail, the fan comprises an impeller 3, preferably a centrifugal impeller, connected directly or indirectly to the motor output shaft 2.

Said impeller 3 is enclosed in a case 4 adapted to channel the flow of aspirated air into a delivery conduit 5 at the end of which there is at least one nozzle 6 for delivering the liquid in spray form.

According to a preferred variant, said conduit 5 comprises a first portion 5a connected to one end of the case 4, which at the opposing end splits into a same number of second portions 5b, each of which is connected to a nozzle 6.

The liquid disinfectant to be atomized is drawn from a specific flask 7 that can be connected to the device by means of an attachment 8, preferably a quick-release attachment.

As mentioned above, said liquid disinfectant may comprise for example a hydrogen peroxide solution in variable percentages from 5% to 15%, preferably with the addition of silver sulfate and other surfactants.

A pump 9 continuously or alternately draws a specific quantity of liquid from the flask and sends it, by means of a pipe 10, to a pre-loading vessel 11.

Said pump 9 is preferably a peristaltic pump but may also be any pump made of materials compatible with the liquid to be transported, and in particular with hydrogen peroxide.

A solenoid valve 12 may be located on said pipe 10, preferably interposed between the flask 7 and the pump 9, to enable the liquid to be drawn from the flask 7.

A management and control system, not shown in the figure, controls both the pump 9 and the solenoid valve 12 to manage the feed of disinfectant into the pre-charging vessel 11.

Preferably, inside said pre-charging vessel 11 there is a level sensor 13, of a mechanical or electronic type, which indicates the level of the liquid inside the vessel to the management and control system, and in turn controls the switching on or off of the pump 9.

At least one siphoning pipe 14 is immersed under the free surface of the liquid in the pre-charging vessel 11 for transporting a quantity of said liquid towards the nozzles 6.

Preferably there is a single pipe 14 feeding each individual nozzle 6.

According to a preferred variant of the invention, said nozzle 6 comprises a head 15 located at the ends of the portions 5*b* of the conduit 5 through which the flow of air coming from the fan is sent. Said head 15 in turn comprises a plurality of passages 16, of a diameter much smaller than the diameter of the conduit 5*b*, arranged in a manner converging on the center of the head. A central hole 17 is made in the head to house the siphoning pipe 14 for the liquid contained in the flask 7.

The number of conduits and their diameter may vary according to the performance of the machine, i.e. the flow of air moved by the fan.

In detail, said pipe is located with its end at the outer edge of the hole 17 on the head 15.

The nozzle with this conformation can aspirate a specific quantity of liquid from the flask 7 and expel it in the form of very small droplets with a diameter of less than 5 microns.

This is achieved thanks to the flow of air that, as it passes through the passages 16, accelerates considerably to create an area of low pressure in the area of the outlet from the central hole 17 where the siphoning pipe 14 is located.

According to the Venturi tube principle, this area of low pressure drags a small quantity of liquid through the siphoning pipe 14 which, when it comes into contact with the flow of turbulent air just outside the head 15, is finely atomized.

According to the invention, there is at least one further pressure pipe 18, connected to the fan unit, and communicating with the inside of the pre-charging vessel 11 to increase the pressure inside it.

To this end, the pre-charging vessel 11, which may be any shape and size, is constituted by a box-like recipient that can be hermetically sealed, for example with a lid 22.

The pressure pipe 18 is preferably located at the top (on the lid 22) or in any case in such a way that it can inject the flow of air into the area between the free surface of the liquid and the lid 22.

For this reason the pre-charging vessel is never completely full but, thanks to the level sensor 12 which keeps the level of the liquid between pre-determined minimum and maximum levels (by continuously or alternately activating the pump 9), there is always a volume of air between the free surface of the liquid and the top surface of the vessel 11.

Said flow of injected air ensures that a pressure is exerted on the free surface of the liquid inside the vessel 11 that is always higher than the atmospheric pressure in the location where the device is located. This greater pressure compresses the liquid, forcing it to rise into the siphoning pipe 14 towards the nozzles 6. In practice, said excess pressure increases the flow of liquid delivered by the nozzle 6 with respect to normal working conditions, thanks to the Venturi tube principle.

By correctly regulating the pressure and flow of air to the pressure conduit 18, it is possible to regulate the variation in the flow of liquid delivered by the nozzle 6.

Advantageously, according to the embodiment shown, said pressure pipe 18e connected to the conduit 5 that carries the air towards the nozzles 6.

In practice, at any point of the conduit 5 is it possible to draw off a certain flow of air which is sent to the pre-charging vessel by means of pressure pipe 18.

This makes it possible to use the motor 2 and the fan connected to it as means for sending the flow of air under pressure to the pre-charging vessel 11.

Since the motor 2, being electrically-powered, generally works at a fixed speed, then the pressure and flow of air drawn off the conduit 5 and sent to the pre-charging vessel 11 are also practically constant.

A characteristic of the invention is therefore that of providing regulating means 19, 29 to allow regulation of the pressure inside the pre-charging vessel 11 and therefore the flow of liquid disinfectant delivered by the nozzles 6.

More specifically, said regulating means 19, 29 are configured to vary the speed, and therefore the pressure, of a given flow of air entering or exiting the pre-charging vessel 11.

According to a first variant of the invention, said regulating means comprise at least one bleed valve 19 that can be adjusted either manually or automatically by the management and control system.

By acting on the opening and closing of the valve 19 it is therefore possible to regulate the excess pressure inside the vessel 11 from a pre-determined minimum value up to a threshold value.

Said valve 19 is preferably located at the end of a bleed pipe 20, which is in turn connected with the inside of the pre-charging vessel, so as to be able to position the valve at an easily accessible point on the device, for example on the outside of the device casing (carter) 21, especially in the case where it is operated manually.

Like the pressure pipe 18, the bleed pipe 20 is also preferably located on the lid 22 so that it only receives the air present between the free surface of the liquid and the top wall of the vessel 11.

Depending on the quantity of air to be bled, it is possible to have several bleed pipes 20, possibly closable with a cap or similar, at least one of which is provided with an adjustable bleed valve 19.

According to another variant of the invention, said regulating means may comprise a regulating valve 29 located directly on pressure pipe 18 entering the pre-charging vessel 11.

Said regulating valve 29, unlike the bleed valve 19, makes it possible to vary the cross-section of pressure pipe 18, and thereby also the speed and pressure of the flow of air entering the pre-charging vessel 11 and consequently the excess pressure inside it.

In detail, when the cross-section of the flow of air is reduced, there is an increase in the speed and a decrease in the pressure of the air.

In this case, the quantity of liquid pushed through the siphoning pipe 14 towards the nozzles 6 is reduced.

Said regulating valve 29 can be used as an alternative to the bleed valve 19 or in conjunction with it to increase regulation sensitivity.

Like the bleed valve 19, the regulating valve 29 is also preferably located on the outside of the device casing 21 so that it can be operated easily without having to remove said casing, when it is operated manually.

Advantageously, according to the invention a further bleed pipe 23 can be channeled inside the liquid container 7 through the attachment 8, passing through the solenoid valve 12.

In this way, a slight excess pressure is also created inside the container 7, which will make it possible both to improve the drawing of the liquid by the pump 9 and to compensate for the contraction of the walls of the container 7 (generally made of a deformable plastic material), which would otherwise occur due to the aspiration and removal of the liquid inside it.

To ensure greater versatility of use for the device, the pre-charging vessel 11 may be provided with an intake pipe 24 at the end of which is located a non-return valve 25 comprising a quick coupling for a pipe.

Said intake pipe 24 may be used for the quick connection of a further pressure pipe 18 in the event that a high excess pressure is required inside the pre-charging vessel 11.

The non-return valve 25 allows the passage of air only towards the inside of the vessel 11 and not vice-versa. The quick coupling allows the connection and removal of the further pipe 18 in just a few seconds, without the need for any specific equipment.

The device described by the present invention enables the effective resolution of the problems that afflict known devices.

Thanks to the pressurization inside the vessel 11 and the presence of the regulating means, valves 19, 29, it is possible to calibrate the machine each time it is used to suit the environmental conditions to ensure that the flow of liquid delivered is determined and constant.

When the device has to be used in environments with very different parameters (for example at very different altitudes, or temperatures or levels of humidity) it is possible to re-calibrate the device by acting on the bleed valve 19 or on the regulating valve 29 to set the desired flow of liquid.

In particular, calibration can be carried out by measuring the total flow emitted by the nozzles and the quantity of liquid consumed in a given period of time.

If, depending on the parameter, this is not at the required level, it is possible to intervene on the regulating means to reset the correct value.

The calibration procedure is therefore simple and quick, and can be carried out directly in the place where the device is to be used, based on the environmental parameters present.

In the most extreme cases, for example at very high altitudes, it is possible to connect a further pressure pipe 18 to the intake pipe 24 to obtain an even greater excess pressure that will compensate for the low environmental pressure.

All these aims are achieved by a device that is of simple construction and reliable, and that does not involve substantial increases in cost compared to known devices.

The present invention, as described and illustrated, may be subject to various modifications and variants, all of which fall within the scope of the invention; furthermore, all the details may be replaced with other technically equivalent elements.

The invention claimed is:

1. Device for the delivery of a liquid in spray form comprising:

an air delivery conduit (5) comprising an inlet end (5*a*) and a discharge end (5*b*);

at least one nozzle (6) located at the discharge end (5*b*) of said air delivery conduit (5), the at least one nozzle (6) comprising air passages (16);

a motor (2) connected to a fan (3,4) adapted to draw a flow of air and send the air into the inlet end (5*a*) of the air delivery conduit (5) and discharge the air at the discharge end (5*b*) of the air delivery conduit (5) to the at least one nozzle (6);

a pre-charging vessel (11) for containing a liquid to be atomized;

at least one siphoning pipe (14) with one end located inside said pre-charging vessel (11) below a free surface of the liquid to be atomized, and an opposing end feeding said at least one nozzle (6) the liquid from said pre-charging vessel (11);

at least one pressure pipe (18) having a first end located within the air delivery conduit (5) and a second end located within the pre-charging vessel (11) above the free surface of the liquid, said at least one pressure pipe (18) thereby connected to said fan (3, 4) to provide a specific amount of pressurized air from the air delivery conduit (5) to the inside of the pre-charging vessel (11) above the free surface of the liquid, the pressurized air providing an excess pressure within the pre-charging vessel (11) that compresses the liquid, forcing the liquid to rise into the at least one siphoning pipe (14) towards the at least one nozzle (6) such that the excess pressure increases the flow of liquid delivered by the at least one nozzle (6), wherein regulating the excess pressure regulates a variation in the flow of liquid delivered by the at least one nozzle (6); and a regulating means (19, 29) adapted to regulate the excess pressure inside said pre-charging vessel (11) wherein said regulating means (19, 29) comprises a management and control system connected to a valve (19, 29), the valve (19, 29) being one of the group consisting of:

i) a bleed valve (19) that is automatically regulated by the management and control system to allow a certain quantity of the air within the pre-charging vessel (11) to be released to the outside of the pre-charging vessel (11) to thereby adjust the excess pressure inside said pre-charging vessel (11), and ii) a regulating valve (29) located on said pressure pipe (18) that is automatically controlled by the management and control system to control the amount of pressurized air from the air deliver conduit (5) entering into the inside of the pre-charging (11) to thereby adjust the excess pressure inside said pre-charging vessel (11), wherein the management and control system is configured to regulate the speed and pressure of a given flow of air entering or exiting said pre-charging vessel (11), to regulate the excess pressure inside the pre-charging vessel (11) from a pre-determined minimum value up to a threshold value to thereby vary the flow of liquid delivered by the at least one nozzle (6).

2. Device for the delivery of a liquid in spray form, according to claim 1, wherein said bleed valve (19) is located at the end of a bleed pipe (20) that communicates with the pre-charging vessel (11).

3. Device for the delivery of a liquid in spray form, according to claim 1, wherein said regulating valve (29) is configured to vary the cross-section for the passage of air in the pressure pipe (18).

4. Device for the delivery of a liquid in spray form, according to claim 1, wherein said pressure pipe is connected to said conduit (5, 5*b*).

5. Device for the delivery of a liquid in spray form, according to claim 1, wherein said regulating means (19, 29) are located on the outside of the device's outer casing (21) so that they can be operated without having to remove said casing.

6. Device for the delivery of a liquid in spray form, according to claim 1, wherein said pre-charging vessel (11) is provided with an intake pipe (24) at the end of which is located a non-return valve (25) comprising a quick coupling for a pipe.

7. Device for the delivery of a liquid in spray form, according to claim 1, wherein said pre-charging vessel (11) can be hermetically sealed by means of a top lid (22).

8. Device for the delivery of a liquid in spray form, according to claim 1, further comprising a container (7) containing said liquid to be delivered that can be removably connected to the device, fitted with a pump (9) adapted to transfer said liquid from said container (7) to the pre-charging vessel (11).

9. Device for the delivery of a liquid in spray form, according to claim 8, wherein said pre-charging vessel (11) is provided with a further bleed pipe (23) connected to said liquid container (7) in order to allow a given flow of air from said pre-charging vessel (11) towards the container.

10. Device for the delivery of a liquid in spray form, according to claim 8, wherein said pump (9) is a peristaltic pump.

11. Device for the delivery of a liquid in spray form, according to claim 1, wherein said nozzle (6) comprises a head (15) provided with a plurality of passages (16) of a diameter smaller than the diameter of the conduit (5, 5*b*) arranged in a manner converging on the center of the head, there being a hole (17) in the center of said head to house the siphoning pipe (14) for the liquid contained in the pre-charging vessel (11).

12. Device for the delivery of a liquid in spray form, according to claim 1, wherein said regulating means comprise at least one of the bleed valve (19) that can be automatically regulated by the management and control system to allow a certain quantity of air to be released to the outside of the pre-charging vessel (11) to thereby adjust the excess pressure inside said pre-charging vessel (11).

13. Device for the delivery of a liquid in spray form, according to claim 1, wherein said regulating means comprise said regulating valve (29) located on said pressure pipe (18) that is automatically controlled by the management and control system to control the amount of pressurized air from the air delivery conduit (5) entering into the inside of the pre-charging vessel (11) to thereby adjust the excess pressure inside said pre-charging vessel (11).

14. A device for the delivery of a liquid in spray form comprising:
   an air delivery conduit (5) comprising an inlet end (5a) and a discharge end (5b);
   at least one nozzle (6) located at the discharge end (5b) of said air delivery conduit (5), the at least one nozzle (6) comprising air passages (16);
   a motor (2) connected to a fan (3, 4) adapted to draw a flow of air and send the air into the inlet end (5a) of the air delivery conduit (5) and discharge the air at the discharge end (5b) of the air delivery conduit (5) to the at least one nozzle (6);
   a pre-charging vessel (11) for containing a liquid to be atomized;
   a siphoning pipe (14) with one end located inside said pre-charging vessel (11) below a free surface of the liquid to be atomized, and an opposing end feeding said at least one nozzle (6) the liquid from said pre-charging vessel (11);
   a pressure pipe (18) having a first end located within the air delivery conduit (5) and a second end located within the pre-charging vessel (11) above the free surface of the liquid, said at least one pressure pipe (18) thereby connected to said fan (3, 4) to provide a specific amount of pressurized air from the air delivery conduit (5) to the inside of the pre-charging vessel (11) above the free surface of the liquid, the pressurized air providing an excess pressure within the pre-charging vessel (11) that compresses the liquid, forcing the liquid to rise into the at least one siphoning pipe (14) towards the at least one nozzle (6) such that the excess pressure increases the flow of liquid delivered by the at least one nozzle (6), wherein regulating the excess pressure regulates a variation in the flow of liquid delivered by the at least one nozzle (6); and
   a regulating means (19, 29) adapted to regulate the excess pressure inside said pre-charging vessel (11) wherein said regulating means (19, 29) comprises a management and control system connected to a valve (19, 29), the valve (19, 29) being one of the group consisting of:
   i) a bleed valve (19) that is automatically regulated by the management and control system to allow a certain quantity of the air within the pre-charging vessel (11) to be released to the outside of the pre-charging vessel (11) to thereby adjust the excess pressure inside said pre-charging vessel (11), and
   ii) a regulating valve (29) located on said pressure pipe (18) that is automatically controlled by the management and control system to control the amount of pressurized air from the air deliver conduit (5) entering into the inside of the pre-charging (11) to thereby adjust the excess pressure inside said pre-charging vessel (11),
   wherein the management and control system is configured to regulate the speed and pressure of a given flow of air entering or exiting said pre-charging vessel (11), to regulate the excess pressure inside the pre-charging vessel (11) from a pre-determined minimum value up to a threshold value to thereby vary the flow of liquid delivered by the at least one nozzle (6).

15. The device for the delivery of a liquid in spray form, according to claim 14, wherein the regulating means (19) comprises said bleed valve (19) and said bleed valve (19) is located at the end of a bleed pipe (20) that communicates with the pre-charging vessel (11).

16. The device for the delivery of a liquid in spray form, according to claim 14, wherein the regulating means said regulating valve (29) and said regulating valve (29) is configured to vary the cross-section for the passage of air in the pressure pipe (18).

17. The device for the delivery of a liquid in spray form, according to claim 14, wherein said regulating means (19, 29) are located on the outside of the device's outer casing (21) so that said regulating means (19, 29) can be adjusted without having to remove said casing.

18. The device for the delivery of a liquid in spray form, according to claim 14, further comprising a container (7) containing said liquid to be delivered that can be removably connected to the device, fitted with a pump (9) adapted to transfer said liquid from said container (7) to the pre-charging vessel (11).

19. The device for the delivery of a liquid in spray form, according to claim 18, wherein said pre-charging vessel (11) is provided with a further bleed pipe (23) connected to said liquid container (7) in order to allow a given flow of air from said pre-charging vessel (11) towards the container.

20. The device for the delivery of a liquid in spray form, according to claim 14, wherein said nozzle (6) comprises a head (15) provided with a plurality of passages (16) of a diameter smaller than the diameter of the conduit (5, 5b) arranged in a manner converging on the center of the head, there being a hole (17) in the center of said head to house the siphoning pipe (14) for the liquid contained in the pre-charging vessel (11).

* * * * *

UNITED STATES PATENT AND TRADEMARK OFFICE
CERTIFICATE OF CORRECTION

PATENT NO.        : 9,662,671 B2
APPLICATION NO.   : 14/401694
DATED             : May 30, 2017
INVENTOR(S)       : Maurizio Pastore and Castiglione Olona Page 1 of 1

It is certified that error appears in the above-identified patent and that said Letters Patent is hereby corrected as shown below:

Column 9, Line 23, "at least one nozzle (6)" should read "a nozzle (6)".
Column 9, Line 24, "the at least one nozzle (6)" should read "the nozzle (6)".
Column 9, Line 30, "at least one nozzle (6)" should read "nozzle (6)".
Column 9, Line 36, "at least one nozzle (6)" should read "nozzle (6)".
Column 9, Line 41, "said at least one pressure pipe (18)" should read "said pressure pipe (18)".
Column 9, Lines 48-49, "the at least one nozzle (6)" should read "the nozzle (6)".
Column 9, Line 50, "the at least one nozzle (6)" should read "the nozzle (6)".
Column 9, Lines 52-53, "the at least one nozzle (6)" should read "the nozzle (6)".
Column 10, Line 12, "deliver conduit (5)" should read "delivery conduit (5)".

Signed and Sealed this
Twenty-third Day of April, 2019

Andrei Iancu
*Director of the United States Patent and Trademark Office*